US 9,295,798 B2

(12) United States Patent
Sartore

(10) Patent No.: US 9,295,798 B2
(45) Date of Patent: Mar. 29, 2016

(54) LARYNGOSCOPIC DEVICE WITH DRUG AND OXYGEN DELIVERY CONDUITS

(71) Applicant: Danny Martin Sartore, Springfield, IL (US)

(72) Inventor: Danny Martin Sartore, Springfield, IL (US)

(*) Notice: Subject to any disclaimer, the term of this patent is extended or adjusted under 35 U.S.C. 154(b) by 0 days.

(21) Appl. No.: 14/509,733

(22) Filed: Oct. 8, 2014

(65) Prior Publication Data

US 2015/0099934 A1 Apr. 9, 2015

Related U.S. Application Data

(60) Provisional application No. 61/888,746, filed on Oct. 9, 2013.

(51) Int. Cl.
*A61B 1/267* (2006.01)
*A61M 16/04* (2006.01)
*A61M 16/14* (2006.01)

(52) U.S. Cl.
CPC ....... *A61M 16/0488* (2013.01); *A61M 16/0486* (2014.02); *A61M 16/14* (2013.01); *A61M 2202/0208* (2013.01); *A61M 2202/048* (2013.01); *A61M 2210/1028* (2013.01)

(58) Field of Classification Search
CPC ............ A61M 16/0488; A61M 16/14; A61M 16/0486; A61M 2202/048; A61M 2202/0208
USPC .......... 600/185, 187, 188, 190, 191, 194, 197
See application file for complete search history.

(56) References Cited

U.S. PATENT DOCUMENTS

| 4,483,337 | A | 11/1984 | Clair |
| 5,060,633 | A | 10/1991 | Gibson |
| 5,402,771 | A | 4/1995 | Pilling |
| 5,551,946 | A * | 9/1996 | Bullard ......................... 600/194 |
| 5,897,489 | A | 4/1999 | Urbanowicz et al. |
| 6,142,144 | A | 11/2000 | Pacey |
| 6,543,447 | B2 | 4/2003 | Pacey |
| 6,655,377 | B2 | 12/2003 | Pacey |
| 6,698,429 | B2 | 3/2004 | Croll et al. |
| 6,764,443 | B1 | 7/2004 | Watson |
| 6,890,298 | B2 | 5/2005 | Berci et al. |
| 8,366,612 | B2 | 2/2013 | Rosenthal |
| 8,529,442 | B2 | 9/2013 | Pacey et al. |

(Continued)

FOREIGN PATENT DOCUMENTS

| EP | 0904726 B1 | 8/2005 |
| EP | 1307131 B2 | 11/2010 |
| WO | 2012097181 A1 | 7/2012 |

OTHER PUBLICATIONS

Glidescope Video Laryngoscopes Quick Reference Guide and User's Manual for GlideScope GVL and Cobalt, Verathon Inc. 2009, 2010.

(Continued)

*Primary Examiner* — Pedro Philogene
*Assistant Examiner* — David C Comstock
(74) *Attorney, Agent, or Firm* — Wendy Thai

(57) ABSTRACT

The invention provides a laryngoscopic device that can be paired with any video baton imaging system to concurrently view the upper airway, deliver oxygen and administer a topical anesthetic to select areas in the airway as needed. The invention also provides a video laryngoscope that includes two conduits, one for delivering oxygen and the other for delivering a pharmaceutical agent to select areas of the airway under real-time visualization.

20 Claims, 4 Drawing Sheets

(56) References Cited

U.S. PATENT DOCUMENTS

| | | |
|---|---|---|
| 2003/0088156 A1 | 5/2003 | Berci et al. |
| 2006/0020171 A1 | 1/2006 | Gilreath |
| 2007/0161863 A1 | 7/2007 | Bentt |
| 2009/0299146 A1 | 12/2009 | McGrath |
| 2010/0261967 A1 | 10/2010 | Pacey et al. |
| 2011/0092773 A1 | 4/2011 | Goldstein |

OTHER PUBLICATIONS

Hagberg, Current Concepts in the Management of the Difficult Airway, Anesthesiology News Special Edition, Oct. 2012.
Healy, A systematic review of the role of videolaryngoscopy in successful orotracheal intubation, BMC Anesthesiology 12:32, 2012.
Heine Master Catalogue Medical 2012, Chapter 3, Laryngoscopes, pp. 71-90.
Jain et al., Comparison of the conventional CMAC and the D-blade CMAC with the direct laryngoscopes in simulated cervical spine injury—amanikin study, Rev. Bras. Anestesiol. Dec. 2013.
KingVISION Video Laryngoscope product brochure, King Systems, A Consort Medical Company, 2010.
LMA MADett® Endotracheal Tube Mucosal Atomization Device product brochure, The Laryngeal Mask Company Limited LMA, 2011.
LMA MADgic Airway product brochure, The Laryngeal Mask Company Limited, 2011.
LMA MADgicWand product brochure, The Laryngeal Mask Company Limited LMA, 2011.
McElwain et al., Comparison of the C-MAC®, Airtraq®, and Macintosh laryngoscopes in patients undergoing tracheal intubation with cervical spine immobilization, British Journal of Anaesthesia, p. 1-7, May 17, 2011.
McGrath® Video Laryngoscope Series 5 product brochure, LMA North America, Inc., 2011.

\* cited by examiner

LARYNGOSCOPIC DEVICE WITH DRUG AND OXYGEN DELIVERY CONDUITS

CROSS-REFERENCE TO RELATED APPLICATIONS

This application claims priority to U.S. Provisional Patent Ser. No. 61/888,746 filed Oct. 9, 2013, which is incorporated herein by reference in its entirety.

BACKGROUND

Tracheal intubation is a procedure for inserting a tube into the trachea for various purposes including to remove blockages from the airway, to open the airway for administering medication or oxygen as needed, or to assist with breathing. During tracheal intubation, a laryngoscope is inserted into the upper airway to aid in locating the larynx and vocal cords and facilitate intubation. Because trachea intubation is invasive and can be extremely uncomfortable, general anesthesia and a muscle relaxant is usually administered prior to the procedure. In emergency situations, however, tracheal intubation is often performed without anesthesia. Similarly, for subjects with neck trauma, injury or abnormal anatomy, a general anesthetic is not administered, as no sedation or minimal sedation is preferred. In these cases, intubation is performed while the subject is awake.

SUMMARY OF THE INVENTION

The invention provides a laryngoscopic device that enables concurrent viewing and delivery of a pharmaceutical or therapeutic agent such as an anesthetic and/or oxygen to one or more select area in the airway of a subject thereby enabling tracheal intubation to be performed with improved safety, with less discomfort and trauma to the subject, and more efficiently. A device of the invention allows an anesthetic and oxygen to be delivered to a select target area in the airway of a patient under real-time visualization as the device is inserted into the upper airway.

In one aspect, the invention provides a laryngoscopic device for use in concurrent viewing of a select area in the airway of a subject and delivery of a pharmaceutical or therapeutic agent to the select area. The laryngoscopic device includes a handle portion adjoining a blade portion and a cavity extending from the handle portion into the proximal region of the blade portion substantially to a light-transmissible window, the cavity being configured to receive a video baton comprising a camera that abuts the light-transmissible window when the baton is placed in the cavity. The laryngoscopic device also includes a first and a second conduit, the first conduit having an atomizer at its distal terminus, each conduit extending substantially along the length of the device and has a distal portion that terminates in an opening adjacent the light transmissible window, each distal portion being positioned so as to not substantially affect the field of view from the window, the distal openings being offset one relative to the other.

In some embodiments, the blade portion of the device is a curved Macintosh blade.

In some embodiments, at least one conduit of the device extends along the right side of the device handle and blade.

In some embodiments, at least one conduit includes a flexible tubing secured to the device at one or more positions along its length using an adhesive, though heat bonding, through one or more retainer clips or collar, or a combination thereof. In some embodiments, the proximal end portion of the flexible tubing extends beyond the proximal end of the device handle so as to be accessible when the laryngoscopic device is placed in the subject's airway such that the handle is within the subject's mouth.

In some embodiments, at least one conduit of the device is integrally formed as part of the body of the laryngoscopic device.

In some embodiments, the first conduit is an anesthetic-delivering tubing having an inner diameter of about 0.4 millimeter to about 1.2 millimeters.

In some embodiments, the first conduit is an anesthetic-delivering tubing, the distal terminus of which comprises a micro spray tip atomizer. In some embodiments, the micro spray tip atomizer includes an opening of about 30 microns.

In some embodiments, the second conduit is an oxygen-delivering tubing having an inner diameter of about 3/16 of an inch.

In some embodiments, the distal opening of the atomizer from which the anesthetic is dispersed is forwardly of the distal opening of the oxygen-delivering tubing thereby enabling the flow of oxygen from the oxygen-delivering tubing to facilitate dispersal of the anesthetic. In some embodiments, the opening of the atomizer from which the anesthetic is dispersed aligns with the edge of the light-transmitting window or is no more than about 2 millimeters forwardly of the light-transmitting window. In some embodiments, the distance between the opening of the atomizer from which the anesthetic is dispersed and the distal opening of the oxygen-delivering tubing is between about 1 millimeter to about 5 millimeters.

In some embodiments, the device is composed of stainless steel, titanium, polycarbonate, silicone, tygon, polyamide, thermoplastic elastomer, polyurethane, polyvinyl chloride, a polyolefin, high- or low-density polyethylene, another rigid or flexible plastic, another metal or any combination thereof.

In some embodiments, the laryngoscopic device is a single-use device.

In another aspect, the invention provides a laryngoscope that includes a laryngoscopic device of the invention and a video baton having a camera at a first end, the video baton being fitted within the cavity of the laryngoscopic device such that the camera abuts the light-transmissible window. In some embodiments, the camera of the video baton is a CMOS camera. In some embodiments, the first conduit includes an anesthetic-delivering tubing, the distal terminus of which includes a micro spray tip atomizer. In some embodiments, the second conduit includes an oxygen-delivering tubing having an inner diameter of about 3/16 of an inch. In some embodiments, the video baton includes a video monitor for displaying real-time images from the camera.

Any feature or combination of features described herein are included within the scope of the present invention provided that the features included in any such combination are not mutually inconsistent as will be apparent from the context, this specification and the knowledge of one of ordinary skill in the art.

Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are illustrative only and not intended to be limiting. Although methods and materials similar or equivalent to those described herein can be used to practice the invention, suitable methods and materials are described below.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Other features and advantages of the invention will be apparent from the following detailed description and from the claims.

DETAILED DESCRIPTION OF THE INVENTION

Figure 1:
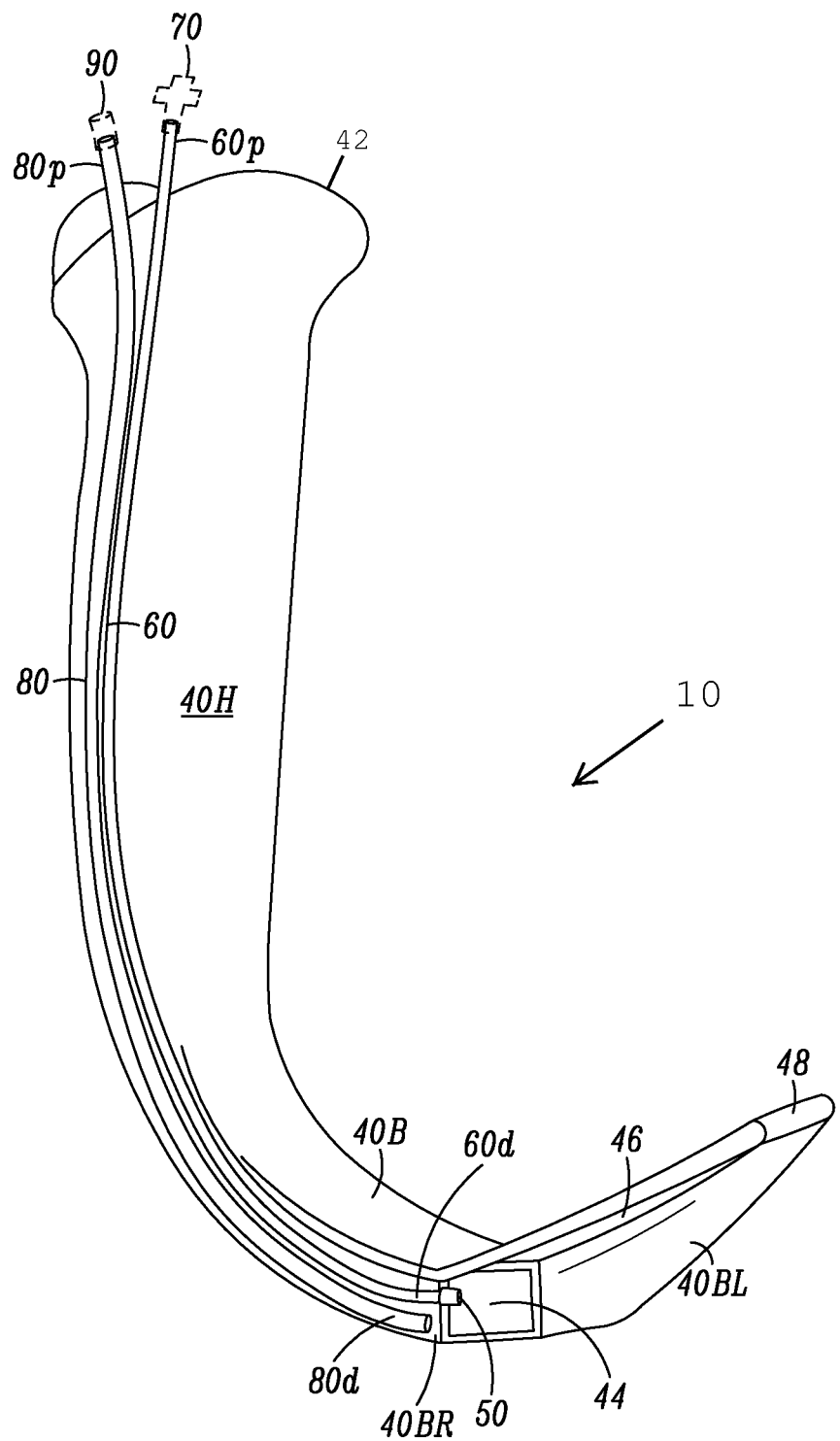
FIG. 1 is a right perspective view of laryngoscopic device 10 of the invention.

The invention provides a laryngoscopic device that enables concurrent viewing and delivery of a pharmaceutical or therapeutic agent such as an anesthetic and/or oxygen to one or more select areas in the airway of a subject thereby enabling tracheal intubation to be performed with improved safety, with less discomfort and trauma to the subject, and more efficiently. The laryngoscopic device of the invention can be used with a video baton as a laryngoscope that allows the user to simultaneously view the airway and deliver a pharmaceutical or therapeutic agent such as an anesthetic and/or oxygen to select regions of the airway. Thus, the invention also provides a laryngoscope in which a laryngoscopic device of the invention is fitted with a video baton for recording images within the airway of a subject.

Handle, Blade and Cavity

A laryngoscopic device of the invention has a handle portion that adjoins a blade portion with a cavity extending from the handle portion into the proximal region of the blade portion substantially to a light-transmissible window. The handle portion can have any size, shape or configuration that facilitates grip and allows the device to be placed inside a subject's mouth. The blade portion of the device can have any size, shape or configuration effective for insertion and manipulation of the airway of a subject as known to those of skilled in the art. The blade portion can be straight or curved. Examples of straight blades include the Cranwall blade, the Jackson blade, the Janeway blade, the Magill blade, the Miller blade, the Phillips blade, the Robertshaw blade, the Seward blade, the Soper blade, the Wis-Hipple blade or the Wisconsin blade. Examples of curved blades include the reduced flange blade, the Macintosh blade, the Parrott blade and the Siker blade. When curved, the blade can include a flat distal region, i.e. the lifter portion, which adjoins the proximal region at a degree of angulation useful for placement in the larynx or throat, for example, about 45, 50, 55, 60 or 65 degrees. The straight or curved blade portion can include a flange as known to those of skilled in the art. The handle portion and blade portion of a laryngoscopic device of the invention can be sized, shaped or configured for human and animal subjects. A laryngoscopic device of the invention can be sized, shaped or configured for use in neonates, infants, children, adults or the obese as known to those of skilled in the art.

The cavity of a laryngoscopic device of the invention is configured to receive a video baton. Video batons for use in laryngoscopes are known in the art and further discussed below. The cavity of a laryngoscopic device of the invention extends through the body of the handle portion into the proximal area of the blade portion, which adjoins the handle portion, and substantially terminates at a light-transmissible window. The light-transmissible window is a vertically-oriented, optically-transparent panel that forms a portion of the blade body. The light-transmissible window is disposed at a region of the blade body most effective for visualizing structures within the airway of a subject. In a straight blade, the light transmissible window can be disposed at the tip of the blade. In a curved blade, the light-transmissible window can be positioned at the bend or angulation point, typically occurring about midpoint of the blade where the proximal portion of the blade adjoins the flat distal portion of the blade that forms the lifter. This recessed position beneath the distal lifter portion of the blade shields the camera from airway fluids, blood or secretions that might otherwise interfere with viewing. The light-transmissible window is constructed of a material that is optically transparent so as to enable a camera such as high-resolution digital camera with a light source such as a light emitting diode that abuts the window to receive image signals from the other side of the window. Thus, the light transmissible window enables the camera of the video baton within the cavity of the blade portion of a laryngoscope of the invention to receive image signals from the airway within which the laryngoscope of the invention is disposed.

First and Second Conduits

A laryngoscopic device of the invention includes a first conduit and a second conduit extending substantially along the length of the device to positions adjacent the light-transmissible window for delivering a pharmaceutical or therapeutical agent to a target area. Each of the conduits is an elongated structure on the body of the laryngoscopic device that has a channel with two open ends through which a gas, compressed gas or fluids can pass. The first conduit is configured with an atomizer at its distal terminus that is effective to disperse a pharmaceutical agent. The positions of the conduits with respect to the light-transmissible window in a laryngoscopic device of the invention enables concomitant visualization and targeted delivery of a pharmaceutical or therapeutic agent to a select area within the airway of a subject.

The first and/or second conduits can be flexible, semi-rigid or rigid tubings secured to the laryngoscopic device along its length using one or more retainers such as rings, clips or clamps. Alternatively, the first and/or second conduits can be flexible, semi-rigid or rigid tubings integrally formed as part of the body of the device. The first and second conduits generally extend along the length of the device, for example, down the right side of the device, along the outer curvature of the device or down the back of the handle then along the right side of the blade, their distal portions terminating in openings positioned near the light-transmissible window for most effective delivery of a pharmaceutical or therapeutic agent to a select target area, while minimally obstructing the field of view from the light-transmissible window. Each distal portion and the corresponding opening can be disposed to the right of the window or underneath the window. For example, the distal portions of the conduits can be positioned one above the other on the right of the window, or side by side beneath the window, or one to the right of the window and the other underneath the window.

Each of the conduits can be sized as appropriate to deliver a pharmaceutical or therapeutic agent such as, for example and without limitation, an anesthetic and oxygen. The conduits can have an internal opening diameter of about 0.001 inches (about 25 micrometers) to about 0.3 inches (or about 8 millimeters), for example, about 0.2, about 0.4, about 0.6, about 0.8, about 1, about 1.5, about 2, about 2.5, about 3, about 3.5, about 4, about 4.5, about 5, about 5.5, about 6, about 6.5 or about 7 millimeters.

The oxygen-delivering conduit can be dimensioned for a select flow rate of oxygen, for example, about 2-6 liters per minute, about 2-8 liters per minute or more than about 8 liters per minute, and can have any internal opening diameter effective for achieving the select flow rate. For example, the oxygen-delivering conduit can have an internal opening diameter of about 4, about 4.5, about 5, about 5.5, about 6, about 6.5, about 7, about 7.5 or about 8 millimeters. The oxygen-delivering conduit can have an internal opening diameter of about 4.765 millimeters or about 3/16 inch.

Similarly, the anesthetic delivering conduit can be sized or selected based the volume, dosage and/or flow rate of a pharmaceutical agent to be administered. The anesthetic delivering conduit can have an internal opening diameter between, for example, about 0.4 to about 1.5 millimeter, with walls of variable thickness, for example, about 1 to about 2 millimeters. Thus, the anesthetic delivering conduit can have an internal opening diameter of about 0.4, about 0.5, about 0.6, about 0.7, about 0.8, about 0.9, about 1.0, about 1.1, about 1.2, about 1.3, about 1.4 or more than about 1.4 millimeters.

Where the conduit is a pharmaceutical agent-delivering conduit, for example, for delivering an anesthetic, the distal portion of the conduit is configured with an atomizer for dispersing the anesthetic into a select area in the airway. Atomizers are known to those of skilled in the art, see, for example, U.S. Pat. No. 6,698,429. An atomizer that can be used in a device of the invention include a micro spray tip having one or more openings, for example, of about 10, about 15, about 20, about 25, about 30, about 35, about 40, about 45 or more microns. Atomizers that can be used in a device of the invention can generate particle sizes between 30-100 microns. Examples of atomizers that can be used in a device of the invention include the LMA MAD Atomization Device or LMA MADett endotracheal tube mucosal atomization device available at www.lmana.com.

In general, the distal portions of the conduits are disposed on the proximal portion of the blade so that their distal openings are in the vicinity of the light-transmissible window to allow real-time visualization or selection of the site of delivery of the pharmaceutical or therapeutic agent, and thus targeted delivery to a selected area in the upper airway. Positioning the conduits so that their distal openings are in the vicinity of the window also minimizes obstruction of the field of view from the window. For example, the conduits can be tubings extending the length of the device, their distal portions secured to the proximal portion of the blade so that their distal openings are in the vicinity of the window. In these embodiments, the distal portion of a tubing can terminate in an opening that aligns with the window, thereby allowing unfettered flow or dispersal of the pharmaceutical or therapeutic agent from the opening and minimal obstruction of the view from the window. The distal portion of the tubing can terminate in an opening that is just forwardly of the window by, for example, about 0.5, about 1, about 1.5, about 2, about 2.5 or about 3 millimeters depending on the size, dimension or configuration of the device, so long as the portion of the tubing forwardly of the window minimally obstructs the field of view from the window. The distal portion of the tubing can terminate in an opening that is just rearwardly of the window by, for example, about 0.5, about 1, about 1.5, about 2, about 2.5 or about 3 millimeters depending on the size, dimension or configuration of the device, so long as the side of the blade forwardly of the opening from which the pharmaceutical or therapeutic agent is released minimally hinders the flow or dispersal of the pharmaceutical or therapeutic agent.

Where the first conduit is an anesthetic-delivering tubing, the distal portion of the tubing/atomizer can be disposed on the device so that its distal opening aligns with the light-transmissible window thereby enabling unfettered flow or dispersal of the anesthetic. The distal portion of the tubing/atomizer can be disposed on the device so that its distal opening is just forwardly of the window by, for example, about 0.5, about 1, about 1.5, about 2, about 2.5 or about 3 millimeters depending on the size, dimension or configuration of the device so as to minimally obstruct the view from the window, and alternatively, the distal portion of the tubing/atomizer can be disposed on the device so that its distal opening is just rearwardly of the window by, for example, about 0.5, about 1, about 1.5, about 2, about 2.5 or about 3 millimeters depending on the size, dimension or configuration of the device so as to minimize hindrance of the flow of the anesthetic by the side of the blade that is forwardly of the opening.

Where one conduit is an anesthetic-delivering conduit, and the other conduit is an oxygen-delivering conduit, the conduits can be positioned one adjacent the other and such that the distal opening of the anesthetic-delivering conduit/atomizer from which an anesthetic is released is forwardly of the distal opening of the oxygen-delivering conduit so that the dispersal of the anesthetic can be facilitated by the flow of oxygen. In these embodiments, the distance between (a) the distal opening of the conduit or atomizer from which the anesthetic is released and (b) the distal opening of the oxygen-delivering conduit can be about 1 millimeter to about 20 millimeters, for example, about 2, about 3, about 4, about 5, about 6, about 7, about 8, about 9, about 10, about 11, about 12, about 13, about 14, about 15, about 16, about 17, about 18 or about 19 millimeters, depending on the oxygen flow rate.

A structure such as the distal portions of the conduits will minimally obstruct the field of view from the light-transmissible window if it lies outside the viewing angle of the camera or light-transmissible window, which can be, for example, about 65, about 60, about 55, about 50, about 45 or about 40 degrees.

The conduits also include proximal portions that extend beyond the proximal end of the larygoscopic device handle by about 0.5 to about 4 inches or more, for example, about 1, about 1.5, about 2, about 2.5, about 3 or about 3.5 inches beyond the proximal end of the device handle. The portions of the conduits extending beyond the laryngoscopic device handle also extend out of the mouth when the device is fully inserted into the upper airway (such that the handle is in the subject's mouth) thereby allowing for user manipulation of the conduits as needed for attachment to connectors such as oxygen connector, nipple-type oxygen connector and Luer lock or Luer tip connector for operating with oxygen supplies or syringes for delivery of pharmaceutical agents. Thus, in some embodiments, the laryngoscopic device of the invention can optionally include an oxygen connector attached to the proximal end of the oxygen-delivering conduit and optionally include a Luer or similar devices attached to the proximal end of the pharmaceutical agent-delivering conduit.

Laryngoscopic Device, Video Baton & Laryngoscope of the Invention

A laryngoscopic device of the invention can be constructed of any materials known to those of skilled in the art. The device can be constructed of an opaque and/or transparent material so long as the light-transmissible window is optically transparent so as to enable the camera within the cavity of the device to receive image signals from the airway. The device can be constructed of a rigid, semi-rigid or flexible material. The device can be rigid, semi-rigid or flexible in part. For example, the handle and blade portion may be rigid or semi-rigid, while the conduits can be rigid, semi-rigid or flexible as is the case for flexible tubings. Where the conduits are tubings, the tubings can have corregations on the inner or outer surface so as to decrease the likelihood of crushing or kinking. The walls of the tubings can be of variable thickness, for example, about 0.5, about 1, about 1.5 or about 2 millimeters thick.

A laryngoscopic device of the invention can be made using methods known to those of skilled in the art including, for example, by injection molding or using a durometer extrusion process to produce those devices having both rigid and flexible portions. As discussed herein, the device handle and blade portions of the device, as well as the conduits can be rigid, semi-rigid or flexible, and the conduits can be integrally formed or separately formed and then secured at one or more positions on the handle and/or blade portions of the device. The laryngoscopic device can be constructed so as to be reusable or constructed of a disposable material for single-use application. Thus, the device can be constructed using one or more metals or metal alloys, as well as one or more natural or synthetic plastics including thermoplastics. Nonlimiting examples of materials that can be used to construct a device of the invention include surgical steel, brass, chrome, stainless steel, titanium, aluminum, fiber optic, polycarbonate, polyvinyl chloride, polyimide, nylon, polyurethane, polyphenlsulfone, polytetrafluorethylene (Teflon), polyester resin, acetal resin, nylon resin and other engineering-type thermoplastics such as acetals. Additional examples of materials that can be used include, without limitation: poly(methyl methacrylate) (PMMA), ultra-high-molecular-weight polyethylene (UHMWPE), Nylon 6, Nylon 6-6, polytetrafluoroethylene (PTFE/Teflon), acrylonitrile butadiene styrene (ABS), polycarbonates (PC), polyamides (PA), polybutylene terephthalate (PBT), polyethylene terephthalate (PET), polyphenylene oxide (PPO), polysulphone (PSU), polyetherketone (PEK), polyetheretherketone (PEEK), polyimides, polyphenylene sulfide (PPS), polyoxymethylene plastic (POM/Acetal), high-density polyethylene, polyvinyl chloride, low-density polyethylene, polypropylene, polyamides, acrylonitrile butadiene styrene, polycarbonate/acrylonitrile butadiene styrene, and polyetheretherketone. Where injection molding is utilized, a device of the invention can be made using a polymer or resin including a thermoplastic (e.g. nylon, polyethylene and polystyrene), thermoset (e.g. epoxy and phenolic) or an elastomer. Where a dual durometer process is utilized, a device of the invention can be made using various combinations of polymers including PVC to PVC, PVC to urethanes, PVC to thermoplastic elastomer (TPE) and polypropylene to thermoplastic rubber (TPR) as known to those of skill in the art. Where transparency is desirable, materials that can be used to construct a device of the invention include, without limitation, transparent plastics such as acrylic (polymethlamethacrylate), butyrate (cellulose acetate butyrate), Lexan (polycarbonate), and PETG (glycol modified polyethylene terphthalate).

The laryngoscopic device can be configured so as to operate with any video baton known to those of skilled in the art. As used herein, the term video baton refers to an imaging system disposed within the body of a laryngoscope for visualizing at least the upper airway of a human or animal subject; the video baton includes a camera operably connected to typically fiberoptic cables for conveying images from the camera to a video system and display. More specifically, a video baton imaging system typically includes a high-resolution, digital camera, and a light source, for example, a CCD or CMOS active pixel sensor video camera and LED, as well as cables for communicating with a video display. Images obtained by a video baton internal of the laryngoscope can be sent to an external monitor/processor through a video cable connecting the video baton to the external monitor, e.g. high-resolution LCD monitor. Alternatively, the video baton can include a built-in videoscreen such as an OLED display disposed above the handle portion. A laryngoscopic device with a first and a second conduit for the delivery of a pharmaceutical or therapeutic agent as provided by the invention can be dimensioned to house any video baton imaging system known to those of skilled in the art for simultaneous viewing of the airway, delivery of oxygen, and targeted administration of an anesthetic to select area as desired. Examples of video baton imaging systems with which a laryngoscopic device of the invention can be paired include the GlideScope Cobalt video baton of Verathon, the handheld imaging systems of King Vision, the portable McGRATH Video Laryngoscope of LMA TELEFLEX and the C-MAC S Imager of Karl Storz. See GLIDESCOPE AVL Single Use Video Laryngoscopes, at http://verathon.com/products/glidescope/avl-single-use (last visited Oct. 7, 2014) and GlideScope AVL Single Use Video Laryngoscope Product Brochure, at http://verathon.com/Portals/0/uploads/ProductMaterials/_gs/AVL2/0900-4331-01-86%20-%20GlideScope%20AVL%20Single%20Use%20Product%20Brochure.pdf (last retrieved Oct. 7, 2014. See also King Vision: Portable Video Laryngoscopes, at http://www.kingsystems.com/medical-devices-supplies-products/airway-management/video-laryngoscopes/ (last visited Oct. 7, 2014) and KingVISION Video Laryngoscope Product Brochure, at http://www.kingsystems.com/wp-content/uploads/2010/09/LIT-101-KV-Brochure_0211.pdf (last retrieved Oct. 7, 2014). See also MCGRATH Series 5 Video Laryngoscope, at http://www.lmana.com/pwpcontrol.php?pwpID:=4489 (last visited Oct. 7, 2014) and McGRATH Video Laryngoscope/Series 5 Product Prochure, available at http://www.lmana.com/files/mcgrath_ems_sales_sheet.pdf (last retrieved Oct. 7, 2014) and C-MAC Video Laryngoscopes, at http://www.airwayworld.com/kart-storz-products/ (last visited Oct. 7, 2014) and C-MAC Single Use Video Laryngoscope, at http://www.airwayworld.com/wp-content/uploads/2013/08/2.-C-MAC-SINGLE-USE.pdf (last retrieved Oct. 7, 2014). Thus, a laryngoscopic device of the invention can have the configuration of any existing video laryngoscopic blade such as, for example, single-use disposable blades for use with the (1) GlideScope AVL Video Laryngoscope of Verathon Medical described above (www.verathon.com), (2) KingVISION Video Laryngoscope of Kingsystems (www.kingsystems.com), (3) the McGRATH Video Laryngoscope designed and manufactured by Aircaft Medical and sold by LMA North America (www.lmana.com), and (4) the C-MAC Video Larngoscopes of Karl Storz (www.airwayworld.com) so long as the device includes two conduits, for example, an oxygen tubing and a tubing with an atomizer at its distal end effective for delivering a pharmaceutical agent such as an anesthetic. And as such, a laryngoscopic device of the invention can be formed by modifying any video laryngoscopic blades known to those of skilled in the art so as to include the two conduits of which one terminates in an atomizer as described herein. Additional laryngoscopic blade configuration that a laryngoscopic device of the invention can resemble or which can be modified to incorporate two conduits of which one terminates in an atomizer as described herein are described in the following patent and patent applications, which are incorporated herein by reference in their entirety: US20140160261, US20100261967, US20090299146, US20060020171, US20030088156, U.S. Pat. No. 6,764,443, U.S. Pat. No. 5,897,489, U.S. Pat. No. 8,366,612, U.S. Pat. No. 6,663,026 and U.S. Pat. No. 8,529,442. A laryngoscopic device and laryngoscope of the invention can also be made using methods and materials known to those of skilled in the art, for example, as described in the following patent and patent applications, which are incorporated herein by reference in their entirety: US20140160261, US20100261967, US20090299146, US20060020171, US6890298, and U.S. Pat. No. 8,529,442.

A laryngoscope of the invention can be used to simultaneously deliver oxygen and a pharmaceutical agent such as an anesthetic as the device is inserted into the upper airway. As such, the conduits can be fitted with connectors at their proximal portions as needed to allow for the transfer of the pharmaceutical or therapeutic agent to the channels for delivery to the airway through the conduits. For example, where one conduit is an oxygen-delivering tubing, the proximal portion of the oxygen-delivering tubing can be fitted with an oxygen tubing connector that allows the tubing to be connected to an oxygen source. Similarly, where the other conduit is a anesthetic-delivering tubing, the proximal end of the anesthetic-delivering tubing can be fitted with a connector such as a female Luer for cooperating with any standard syringe thereby allowing for the transfer of a select dose of the anesthetic to the anesthetic-delivering tubing.

Realtime Viewing of the Upper Airway with Concommitant Targeted Administration of a Topical Anesthetic and Oxygen A laryngoscopic device of the invention can be fitted with a video baton imaging system thereby forming a laryngoscope that can be used to concurrently examine the upper airway and deliver a pharmaceutical and/or therapeutic agent as needed.

More specifically, a laryngoscopic device of the invention having an oxygen-delivering conduit such as an oxygen-delivering tubing and a pharmaceutical agent-delivering conduit such as an anesthetic-delivering tubing with atomizer or micro spray tip at its distal end can be pair with a video baton as described above and known to those of skilled in the art. The resulting laryngoscope of the invention can be attached to an external video system and monitor through a video cable if needed (where the video baton does not include an integral video monitor), as well as to an oxygen source prior to its use. The proximal region of oxygen-delivering tubing can be attached to an oxygen source through an oxygen tubing connector. Similarly, the proximal region of the anesthetic-delivering tubing can be fitted with a female Luer to allow for delivery of the anesthetic using a syringe.

The laryngoscope is then inserted into the subject's mouth thereby allowing for viewing real-time video images of the subject's airway with simultaneous delivery of supplemental oxygen as needed and at flow rates determined by the performing clinician. As the laryngoscope descends into the subject's airway, the areas to be topically anesthetized, for example, the pharyngeal/laryngeal structures come into view and into the vicinity or delivery range of the atomizer adjacent the video window. Topicalization (topical anesthetization) is accomplished by injecting the clinician's desired concentration and volume of an anesthetic solution via the Luer syringe adapter connected to the proximal end of the anesthetic-delivering tubing thereby delivering the anesthetic to the desired/targeted structures being visualized. When the desired areas have been adequately anesthetized to the performing clinician's satisfaction, another procedure, for example, endotracheal intubation can be performed under real-time video visualization with the clinician's endotracheal tube of choice as clinically indicated. The real-time visualization and targeted application of oxygen and local anesthetic(s) minimizes time required to perform the intubation, reduces likelihood of trauma to the airway and laryngeal structures, improves patient comfort and ultimately improves patient safety. The immediate and positive recognition by the performing clinician of correct placement of the endotracheal tube in the trachea also improves patient safety.

In short, the device allows the user to provide oxygen, as well as selectively targeted particular areas in the airway for application of a topical or local anesthetic as the laryngoscope of the invention is inserted into the upper airway for visualization.

Specific embodiments of the invention are described in the following examples, which do not limit the scope of the invention described in the claims.

Example

FIG. 1 illustrates an embodiment of a laryngoscopic device of the invention. Device 10 includes handle portion 40H adjoining curved blade portion 40B. Blade portion 40B includes right distal side 40BR, left distal side 40BL, light-transmissible window 44, and lifter 46 extending to tip 48. Device 10 also includes tube 60 and tube 80 disposed on device 10 along its the right side.

Figures 2A, 2B:
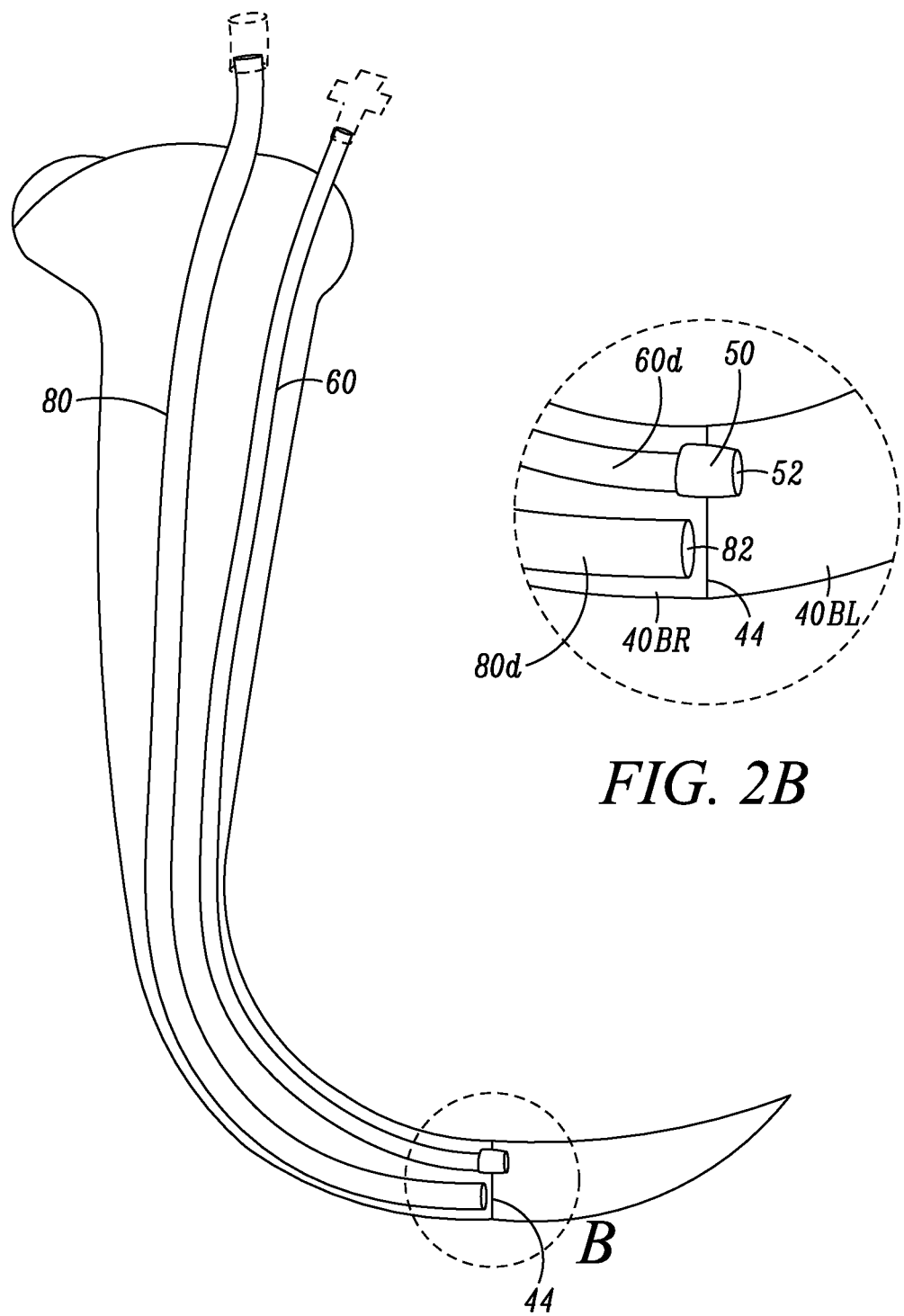
FIGS. 2A-2B are two views of a laryngoscopic device of the invention including a right side view (2A) and an enlarged view of section B (2B)

Tube 60 includes distal portion 60*d*, which is secured to device 10 on its right distal side 40BR adjacent light transmissible window 44, and proximal portion 60*p*, which extends about 0.5 to about 4 or more inches beyond proximal edge 42 of device handle 40H. Distal portion 60*d* is attached to atomizer 50, which allows a metered dose of the pharmaceutical agent in tube 60 to be dispersed to a select area in the airway of a subject. Distal portion 60*d* with atomizer 50 is attached to right distal side 40BR device 10 such that the forward edge of atomizer 50 with opening 52 aligns with or is just forwardly of light transmissible window 44 (FIGS. 2A & 2B), thereby enabling efficient dispersal of the pharmaceutical agent from atomizer 50 without substantially obstructing the field of view of window 44. Proximal portion 60*p* can be attached to female Luer 70 to enable delivery of an anesthetic using a syringe (FIG. 1).

Tube 80 includes distal portion 80*d*, which is also secured to device 10 on its right distal side 40BR adjacent light transmissible window 44, and proximal portion 80*p*, which extends about 0.5 to about 4 or more inches beyond proximal edge 42 of device handle 40H. Distal portion 80*d* is attached to distal side 40BR beneath distal portion 60*d* such that opening 82 of distal portion 80*d* is offset rearwardly relative to opening 52 of atomizer 50 by about 1 millimeter to about 10 millimeters, for example, about 3 millimeters (FIGS. 2A & 2B), thereby enabling the flow of oxygen from tube 80 to aid in dispersing the pharmaceutical agent from atomizer 50.

Proximal portion 80p can be attached to oxygen tube connector 90 to enable connection with an oxygen source (FIG. 1).

Tube 60, which is dimensioned for delivering a pharmaceutical agent such as an anesthetic, has a smaller diameter than tube 80, which is dimensioned to achieve a select oxygen flow rate.

Figures 3A, 3B:
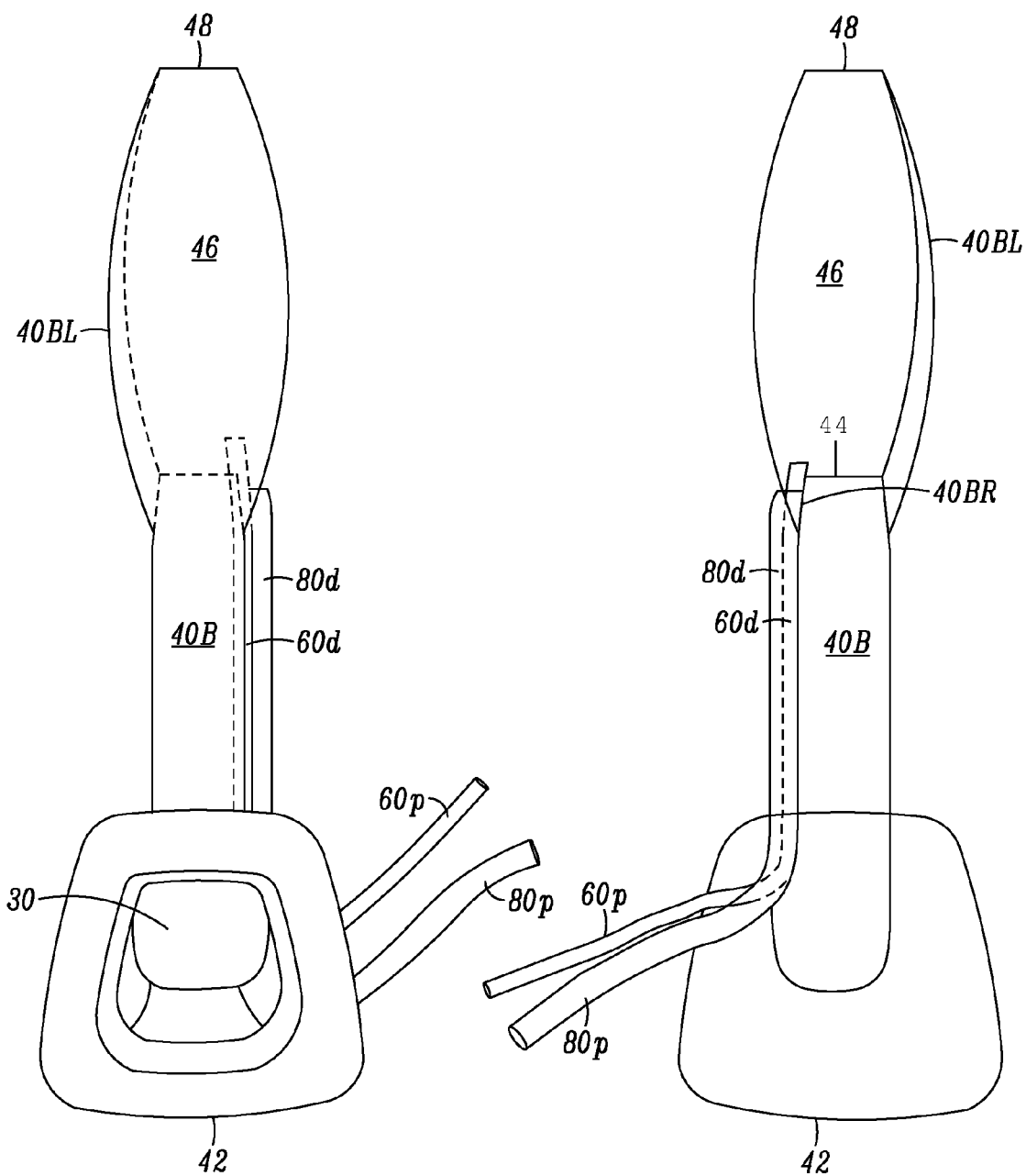
FIGS. 3A-3B are two views of a laryngoscopic device of the invention including a top side view (3A) and a bottom side view (3B).

FIGS. 3A and 3B provide a top-down and bottom-up view, respectively, of an embodiment of a laryngoscopic device of the invention. The device includes a cavity 30, which extends from handle portion 40H into the proximal region of blade portion 40B substantially to light-transmissible window 44 (FIG. 3A).

Figure 4:
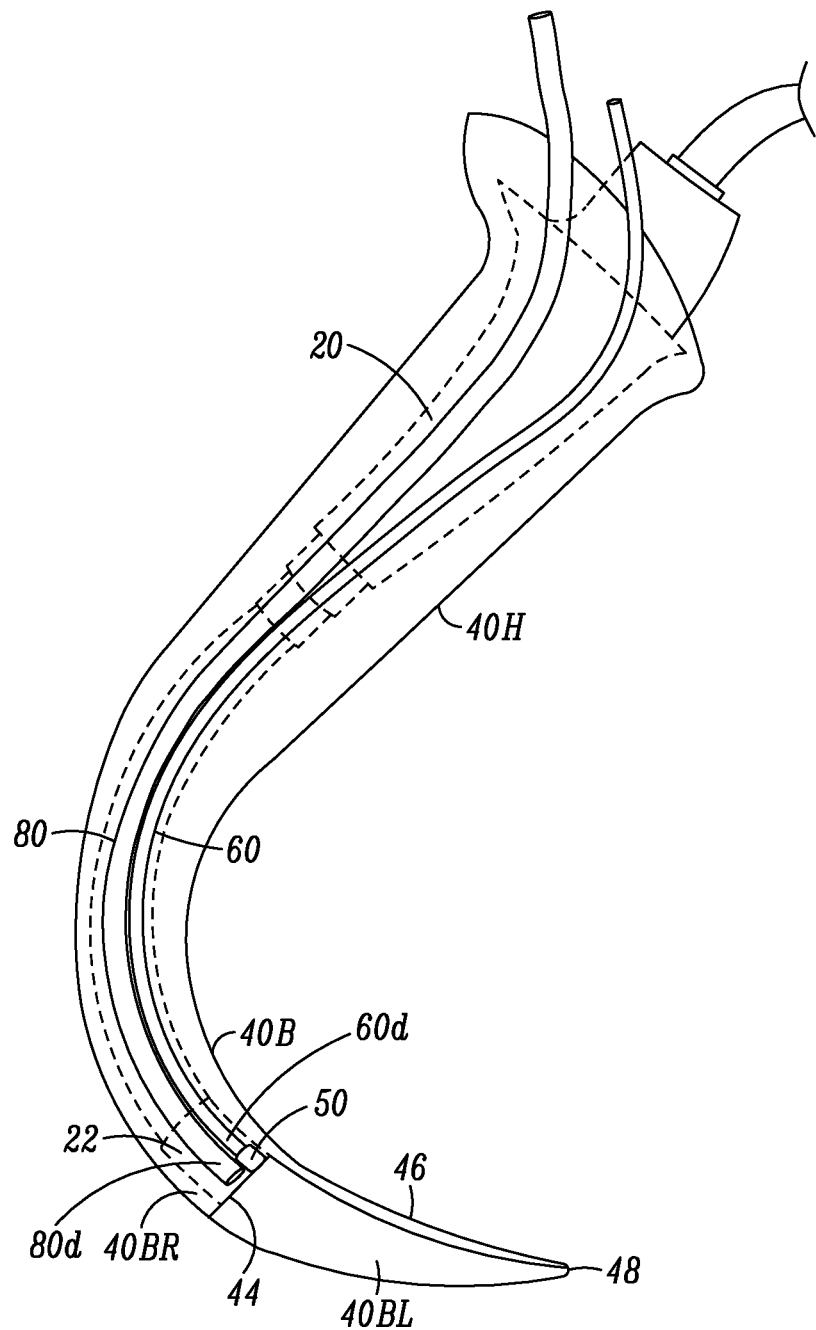
FIG. 4 is a view of a laryngoscope of the invention illustrating the position of the video baton within the cavity of a laryngoscopic device of the invention.

FIG. 4 provides a right side view of an embodiment of a laryngoscope of the invention. In this embodiment, a laryngosopic device of the invention is paired with video baton 20 having camera 22. Video baton 20 is disposed in the cavity that extends through the handle portion to the proximal portion of the blade substantially to video window 44 of the laryngoscopic device of the invention. As shown in FIG. 4, video camera 22 abuts light-transmissible window 44 thereby enabling video camera 22 to receive images through light-transmissible window 44, which can have an antifogging mechanism. In this embodiment, the opening or edge of atomizer 50 on the distal portion of the anesthetic-delivering conduit is aligned with the video window 44, while the opening of distal portion 80d of the oxygen-delivering conduit 80 is disposed rearwardly of the atomizer opening enabling the flow of oxygen from the oxygen-delivering conduit 80 to facilitate dispersal of anesthetic from atomizer 50.

OTHER EMBODIMENTS OF THE INVENTION

While the invention has been described in conjunction with the detailed description, the foregoing description is intended to illustrate and not limit the scope of the invention, which is defined by the scope of the claims. Other aspects, advantages, and modifications are within the scope of the following claims.

The terms and expressions that have been employed are used as terms of description and not of limitation, and there is no intent in the use of such terms and expressions to exclude any equivalent of the features shown and described or portions thereof. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. In addition, the invention has been described broadly and generically herein. Each of the narrower species and subgeneric groupings falling within the generic disclosure also form part of the invention.

As used herein and in the appended claims, the singular forms "a," "an," and "the" include plural reference unless the context clearly dictates otherwise. Under no circumstances may the patent application be interpreted to be limited to the specific examples or embodiments or methods specifically disclosed herein.

What is claimed is:

1. A laryngoscopic device for use in concurrent viewing of a select area in the airway of a subject and delivery of a therapeutic agent to the select area, the device comprising:

(a) a handle portion adjoining a blade portion and a cavity extending from the handle portion into the proximal region of the blade portion substantially to a light-transmissible window, the cavity being configured to receive a video baton comprising a camera that abuts the light-transmissible window when the baton is placed in the cavity;

(b) the device further comprising a first and a second conduit, the first conduit comprising an atomizer at its distal terminus, each conduit extending substantially along the length of the device and comprising a distal portion that terminates in an opening adjacent the light transmissible window, each distal portion being positioned so as to not substantially affect the field of view from the window, the distal openings being offset one relative to the other.

2. The laryngoscopic device of claim 1, wherein the blade portion comprises a curved Macintosh blade.

3. The laryngoscopic device of claim 2, wherein at least one conduit extends along the right side of the device handle and blade.

4. The laryngoscopic device of claim 3, wherein at least one conduit comprises flexible tubing secured to the device at one or more positions along its length using an adhesive, though heat bonding, through one or more retainer clips or collar, or a combination thereof.

5. The laryngoscopic device of claim 4, wherein the proximal end portion of the flexible tubing extends beyond the proximal end of the device handle so as to be accessible when the laryngoscopic device is placed in the subject's airway such that the handle is within the subject's mouth.

6. The laryngoscopic device of claim 3, wherein at least one conduit is integrally formed as part of the body of the laryngoscopic device.

7. The laryngoscopic device of claim 1, wherein the first conduit comprises an anesthetic-delivering tubing having an inner diameter of about 0.4 millimeter to about 1.2 millimeters.

8. The laryngoscopic device of claim 1, wherein the first conduit comprises an anesthetic-delivering tubing, the distal terminus of which comprises a micro spray tip atomizer.

9. The laryngoscopic device of claim 8, wherein the micro spray tip atomizer comprises an opening of about 30 microns.

10. The laryngoscopic device of claim 8, wherein the second conduit comprises an oxygen-delivering tubing having an inner diameter of about 3/16 of an inch.

11. The laryngoscopic device of claim 10, wherein the distal opening of the atomizer from which the anesthetic is dispersed is forwardly of the distal opening of the oxygen-delivering tubing thereby enabling the flow of oxygen from the oxygen-delivering tubing to facilitate dispersal of the anesthetic.

12. The laryngoscopic device of claim 11, wherein the opening of the atomizer from which the anesthetic is dispersed aligns with the edge of the light-transmitting window or is no more than about 2 millimeters forwardly of the light-transmitting window.

13. The laryngoscopic device of claim 11, wherein the distance between the openings is between about 1 millimeter to about 5 millimeters.

14. The laryngoscopic device of claim 1, which comprises stainless steel, titanium, polycarbonate, silicone, tygon, polyamide, thermoplastic elastomer, polyurethane, polyvinyl chloride, a polyolefin, high- or low-density polyethylene, another rigid or flexible plastic, another metal or any combination thereof.

15. The laryngoscopic device of claim 1, which is a single-use device.

16. A laryngoscope comprising the laryngoscopic device of claim 1 and a video baton comprising a camera at a first end, the video baton being fitted within the cavity of the laryngoscopic device such that the camera abuts the light-transmissible window.

17. The laryngoscope of claim 16, wherein the camera is a CMOS camera.

18. The laryngoscope of claim 17, wherein the first conduit comprises an anesthetic-delivering tubing, the distal terminus of which comprises a micro spray tip atomizer.

19. The laryngoscope of claim 18, wherein the second conduit comprises an oxygen-delivering tubing having an inner diameter of about 3/16 of an inch.

20. The laryngoscope of claim 16, wherein the video baton comprises a video monitor for displaying real-time images from the camera.

* * * * *